(12) United States Patent
Lee et al.

(10) Patent No.: US 8,003,140 B1
(45) Date of Patent: Aug. 23, 2011

(54) HERBAL MEDICINAL COMPOSITION AND EXTRACT THEREOF FOR INDUCING PROLIFERATION OF CRANIAL NERVE CELLS AND METHOD OF MANUFACTURING THE SAME

(75) Inventors: Chen-Yu Lee, Taipei (TW); Hsiu-Chin Ho, Sanchong (TW); Cheng-Fu Chang, Taipei (TW); Yi Lin Chen, Sanchong (TW)

(73) Assignee: Chen-Yu Lee, Taipei (TW)

( * ) Notice: Subject to any disclaimer, the term of this patent is extended or adjusted under 35 U.S.C. 154(b) by 0 days.

(21) Appl. No.: 12/929,143

(22) Filed: Jan. 4, 2011

(30) Foreign Application Priority Data

Sep. 24, 2010 (TW) .................................. 099132366

(51) Int. Cl.
| | |
|---|---|
| *A61K 36/00* | (2006.01) |
| *A61K 36/284* | (2006.01) |
| *A61K 36/076* | (2006.01) |
| *A61K 36/236* | (2006.01) |
| *A61K 36/232* | (2006.01) |
| *A61K 36/804* | (2006.01) |
| *A61K 36/714* | (2006.01) |
| *A61K 36/539* | (2006.01) |
| *A61K 36/481* | (2006.01) |
| *A61K 36/25* | (2006.01) |
| *A61K 36/537* | (2006.01) |
| *A61K 36/48* | (2006.01) |
| *A61K 36/906* | (2006.01) |
| *A61K 36/54* | (2006.01) |
| *A61K 36/258* | (2006.01) |

(52) U.S. Cl. ........ 424/725; 424/746; 424/757; 424/756; 424/739; 424/728

(58) Field of Classification Search ........................ None
See application file for complete search history.

*Primary Examiner* — Qiuwen Mi

(74) *Attorney, Agent, or Firm* — Bacon & Thomas, PLLC

(57) ABSTRACT

A herbal medicinal composition, an extract thereof, and a method of manufacturing the same are disclosed. The herbal medicinal composition may be used to induce proliferation of cranial nerve cells, and it includes: 1.5-6 parts by weight of Salvia Radix, 1.5-6 parts by weight of Atractylodis Rhizoma, 1.5-6 parts by weight of *Poria*, 1.5-6 parts by weight of Glycyrrhizae Radix, 1.5-6 parts by weight of Angelicae Radix, 1.5-6 parts by weight of Paeoniae (Ovatae) Radix Rubra, 1.5-6 parts by weight of Ligustici Rhizoma, 1.5-6 parts by weight of Rehmanniae Radix, 2.5-10 parts by weight of Aconiti Tuber, 1.5-6 parts by weight of Zingiberis Rhizoma, 1.5-6 parts by weight of Scutellariae Radix, 2.5-10 parts by weight of Cinnamon Seed, 10-40 parts by weight of Astragali Radix, 1.5-6 parts by weight of Cinnamomum Ramulus, and 1.5-6 parts by weight of Ginseng Radix.

6 Claims, 3 Drawing Sheets

(A)

(B)

(C)

(D)

(A)  (B)

(C)  (D)

(A)

(B)

(C)

(D)

(E)

HERBAL MEDICINAL COMPOSITION AND EXTRACT THEREOF FOR INDUCING PROLIFERATION OF CRANIAL NERVE CELLS AND METHOD OF MANUFACTURING THE SAME

BACKGROUND OF THE INVENTION

1. Field of the Invention

The present invention relates to a herbal medicinal composition, an extract thereof, and a method for manufacturing the same and, more particularly, to a herbal medicinal composition and an extract thereof for inducing proliferation of cranial nerve cells and a method for manufacturing the same.

2. Description of Related Art

In developed countries, cerebrovascular diseases are one of the ten leading causes of death and even survivors suffer critically with disabled limbs. Therefore, medical treatment and care for both acute and chronic cerebrovascular diseases have already become burdens of society and countries. Stroke is one of cerebrovascular diseases and generally happens in aged people. As the structure of the population tends to advanced age, the incidence of stroke rapidly increases.

The common stroke is classified into ischemia-type stroke and hemorrhage-type stroke. The ratio of the ischemia-type stroke is about 80% and that of the hemorrhage-type stroke is about 20%. Since strokes strike very suddenly, irreversible lesions in the brain of a patient and even death will occur if the patient is not delivered to a hospital for immediate treatment. Therefore, if treatment can be applied to a patient suffering a stroke within an efficacious period to prevent irreversible lesion in his/her brain, death and disablement rates can be decreased so as to reduce difficulty for rehabilitation after healing and further to advance the quality of life of the patient.

Currently, anti-thrombotic therapy and anti-coagulation therapy are used for the prophylaxis and treatment for ischemia-type stroke. The anti-thrombotic therapy generally used for strokes resulted from brain infarction can prevent strokes from being more severe and restrict thrombi in the artery so as to avoid spread of the thrombi to other regions. Besides, clinical reports show that anti-coagulation therapy may cause undesired bleeding in the region injured by strokes in many patients, and thus the anti-coagulation therapy is used in a reduced rate manner. Furthermore, for the treatment of ischemia-type stroke, the important things are active elimination of acute causes inducing stroke, reflow and perfusion of blood in brain vessels (for example, utilizing thrombolytic agents in veins or arteries) as quickly as possible, and the reduction of death of brain cells by neuron protective agents.

However, the brain cells' tolerance of ischemia is very poor and thus lesions of neurons generally become irreversible before the patients are delivered to hospital for treatment. Accordingly, it is extremely important to increase tolerance of blood and oxygen deficiency and to alleviate injuries of blood and oxygen deficiency to brain neurons.

It has been known for a long time that the central nervous system does not have a characteristic of self-regeneration. In detail, neural stem cells are not contained in the neurons of the central nervous system of adult mammals and thus the neurons do not regenerate after exposure to diseases or injuries. However, research has evidenced that neural stem cells exist in the central nervous system currently. These neural stem cells can be isolated from different regions of hippocampus, ependyma, and so forth. Hence, it is evidenced that neural stem cells exist in the brain of adult mammals and they have the following characteristics of abundant proliferation in vitro and differentiation into neurons and glia cells.

Although functions of the neurons and glia cells in situ regenerated from the neural stem cells are still not clarified, the neural stem cells have potential to be used for treatment of chronic stroke, neurodegeneration, and so forth because of their pluripotency. However, no efficacious medicines can activate differentiation of neural stem cells into neurons and glia cells to replenish brain cells in injured regions at present. Therefore, there is an urgent need to find safe and efficacious medicines or methods for treating strokes.

SUMMARY OF THE INVENTION

The object of the present invention is to provide a herbal medicinal composition which is extracted by a method for manufacturing a herbal medicinal extract. The herbal medicinal extract obtained can be used to induce proliferation of brain cells and thus is suitable for the treatment of strokes.

To achieve the object, an aspect of the present invention provides a herbal medicinal composition which includes: 1.5-6 parts by weight of Salvia Radix (*Salvia Miltiorrhiza* Bge), 1.5-6 parts by weight of Atractylodis Rhizoma (*Atractylodes lancea* De Candolle), 1.5-6 parts by weight of *Poria* (*Poria cocos* (SCHW.) WOLF.), 1.5-6 parts by weight of Glycyrrhizae Radix (*Glycyrrhiza uralensis* Fischer et DC), 1.5-6 parts by weight of Angelicae Radix (*Angelica sinensis* Diels), 1.5-6 parts by weight of Paeoniae (Ovatae) Radix Rubra (*Paeonia veitchii* Lynch.), 1.5-6 parts by weight of Ligustici Rhizoma (*Ligusticum chuanxiong* Hortorum), 1.5-6 parts by weight of Rehmanniae Radix (*Rehmannia glutinosa* Libosch. f. hueichingensis (Chao et Schih) Hsiao), 2.5-10 parts by weight of Aconiti Tuber (*Aconitum carmichaeli* Debx. Sieb.), 1.5-6 parts by weight of Zingiberis Rhizoma (*Zingiber officinale* Roscoe), 1.5-6 parts by weight of Scutellariae Radix (*Scutellaria baicalensis* Georgi), 2.5-10 parts by weight of Cinnamon Seed (*Cinnamomum cassia* Presl), 10-40 parts by weight of Astragali Radix (*Astragalus membranaceus* Bunge), 1.5-6 parts by weight of Cinnamomum Ramulus (*Cinnamomum cassia* Presl), and 1.5-6 parts by weight of Ginseng Radix (*Panax ginseng* C. A. MEYER).

Another aspect of the present invention provides a method for manufacturing a herbal medicinal extract, comprising the following steps: mixing 1.5-6 parts by weight of Salvia Radix, 1.5-6 parts by weight of Atractylodis Rhizoma, 1.5-6 parts by weight of *Poria*, 1.5-6 parts by weight of Glycyrrhizae Radix, 1.5-6 parts by weight of Angelicae Radix, 1.5-6 parts by weight of Paeoniae (Ovatae) Radix Rubra, 1.5-6 parts by weight of Ligustici Rhizoma, 1.5-6 parts by weight of Rehmanniae Radix, 2.5-10 parts by weight of Aconiti Tuber, 1.5-6 parts by weight of Zingiberis Rhizoma, 1.5-6 parts by weight of Scutellariae Radix, 2.5-10 parts by weight of Cinnamon Seed, 10-40 parts by weight of Astragali Radix, and 1.5-6 parts by weight of Cinnamomum Ramulus to form a mixture; and extracting the mixture with water under heating to give an extract and then mixing the extract with 1.5-6 parts by weight of Ginseng Radix.

In the abovementioned method for manufacturing a herbal medicinal extract, the Ginseng Radix is powdered.

Further another aspect of the present invention provides a herbal medicinal extract which is manufactured by the method described above.

The herbal medicinal composition and extract of the present invention delineated above can be used to reduce considerable expression of glial fibrillary acidic protein (GFAP) resulted from ischemia caused by infarction of a brain artery. In other words, proliferation of neuroglia cells is decreased and expression of neuronal nuclei (NeuN) is simultaneously promoted, i.e. to induce proliferation of brain neurons. Besides, expression of caspase-3 in the peripheral brain cells of ischemic regions is also inhibited. In other words, execution of apoptosis is blocked in the peripheral brain cells of ischemic regions.

Furthermore, in the herbal medicinal composition delineated above, the Salvia Radix is preferably in an amount of 2.25-4.5 parts by weight; the Atractylodis Rhizoma is preferably in an amount of 2.25-4.5 parts by weight; the *Poria* is preferably in an amount of 2.25-4.5 parts by weight; the Glycyrrhizae Radix is preferably in an amount of 2.25-4.5 parts by weight; the Angelicae Radix is preferably in an amount of 2.25-4.5 parts by weight; the Paeoniae (Ovatae) Radix Rubra is preferably in an amount of 2.25-4.5 parts by weight; the Ligustici Rhizoma is preferably in an amount of 2.25-4.5 parts by weight; the Rehmanniae Radix is preferably in an amount of 2.25-4.5 parts by weight; the Aconiti Tuber is preferably in an amount of 3.75-7.5 parts by weight; the Zingiberis Rhizoma is preferably in an amount of 2.25-4.5 parts by weight; the Scutellariae Radix is preferably in an amount of 2.25-4.5 parts by weight; the Cinnamon Seed is preferably in an amount of 3.75-7.5 parts by weight; the Astragali Radix is preferably in an amount of 15-30 parts by weight; the Cinnamomum Ramulus is preferably in an amount of 2.25-4.5 parts by weight; and the Ginseng Radix is preferably in an amount of 2.25-4.5 parts by weight.

Among the herbal medicinal materials mentioned above, the Angelicae Radix and the Ligustici Rhizoma is immersed in an edible alcohol, and the Aconiti Tuber is processed under heating to reduce its toxicity.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
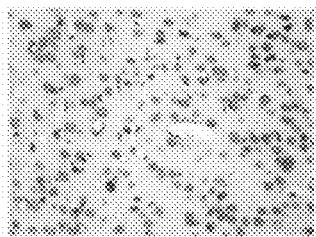
FIG. 1 is an immunohistostaining photograph of glial fibrillary acidic protein (GFAP) showing growth condition of neuroglia cells, in which (A) shows a normal group, (B) shows a control group, and (C) and (D) show the group fed with an extract of Example 1; and reddish brown indicates positive result and cyanosis indicates cell nuclei.
Figure 1:
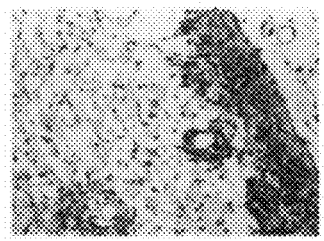
Figure 1:
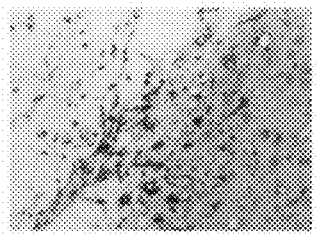
Figure 1:
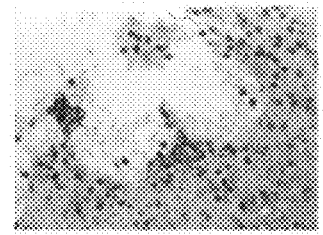

According to the specific embodiments illustrating the practice of the present invention, a person having ordinary skill in the art can easily understand other advantages and efficiency of the present invention through the content disclosed therein. The present invention can also be practiced or applied by other variant embodiments. Many other possible modifications and variations of any detail in the present specification based on different outlooks and applications can be made without departing from the spirit of the invention.

Example 1

Salvia Radix (11.25 g), Atractylodis Rhizoma (11.25 g), Poria (11.25 g), Glycyrrhizae Radix (11.25 g), Angelicae Radix (11.25 g), Paeoniae (Ovatae) Radix Rubra (11.25 g), Ligustici Rhizoma (11.25 g), Rehmanniae Radix (11.25 g), Aconiti Tuber (18.75 g), Zingiberis Rhizoma (11.25 g), Scutellariae Radix (11.25 g), Cinnamon Seed (18.75 g); Astragali Radix (75 g), and Cinnamomum Ramulus (11.25 g) were cut into slices if necessary, and then heated with water (1200 g) at 90° C. or more for 60 to 90 minutes to form an extract (450 g). Herbal dregs were removed from the extract and then the extract was mixed with powders of Ginseng Radix (11.25 g).

Test Example

<Breeding of Experimental Animals>

Every six Sprague-Dawley (SD) rats were enclosed in a cage and fed with sterilized water and feedstuffs. The breeding conditions were constant 22° C. and 12-hours illumination. The rats were bred for an accommodation period of 7 days before they were experimented on.

<Grouping of the Experimental Animals>

Some of the bred SD rats were randomly grouped into a normal group (sham), and the residues were treated with brain ischemia in which artery ligation and reperfusion of blood were performed in order. If the treated rats successfully revived, the reviviscent rats were randomly grouped into a control group and an experimental group.

<Ischemia Model Caused by Artery Ligation and then Reperfusion of Blood (ischemia-reperfusion)>

Ligation of right middle cerebral artery (RMCA) and bilateral carotid was used to cause brain infarction and is described as follows. After the SD rats were anesthetized for ligation with chloralhydrate (0.4 g/kg) by intraperitoneal injection (i.p.), a stroke was caused with 10-O nylon thread in the right cerebral artery of the rats and a burrhole (1 mm in diameter) was formed in right frontal bone above parietal lobe whereafter a photodetector (0.45 mm in diameter) was arranged therein for stereotaxis. The photodetector (0.45 mm in diameter) was used together with a laser Doppler flowmeter to detect the blood flow of the cerebral cortex during the ligation. After 60 minutes, the ligation of right middle cerebral artery (RMCA) and bilateral carotid was removed and reperfusion thereof was executed. Then, the rats were estimated and treated. In addition, during the anesthetization of the rats, a hot pad was used to keep the rats at 37° C.

<Feeding of the Experimental Animals>

The rats successfully treated with the surgical operation of the ischemic stroke were randomly grouped into a control group and an experimental group. The normal group (sham) and the experimental group were orally fed with the extract of Example 1 twice everyday posterior to the operation. The control group was fed with normal saline (5 ml/d). The experimental group was fed in an amount of the extract calculated as follows: the dose (g/Kg)=human dose (g)×0.018/ the body weight of the experimental animal (Kg). Each group was fed with normal saline or the extract for 4 weeks.

<Immunohistochemistry>

The rats were observed for 28 days and then sacrificed to give the brain. The brain was paraffin-embedded and then cut into tissue slices. Before immunohistochemistry, the paraffin had to be removed. First, the cut brain slices were immersed in xylene for 10 minutes for removal of the paraffin and then processed by the following steps in sequence: immersing in 100% ethanol, 95% ethanol, and then in 75% ethanol respectively for 3 seconds, and finally in double distilled water (ddH$_2$O) for 3 seconds.

Subsequently, the washing process was performed. The cut brain slices were shaking-washed with 1×PBS for 5 minutes twice, immersed in 1×PBS containing 0.3% Triton for 10 minutes and then in 3% H$_2$O$_2$ at room temperature for 5 minutes, and finally shaking-washed with 1×PBS containing 0.05% Triton X-100 used as a rinse buffer for 5 minutes twice to remove H$_2$O$_2$.

Before the addition of an antibody, the cut brain slices were treated with blocking so as to avoid the unspecific binding of the antibody. The cut brain slices were covered with 1×PBS containing 5% skim milk under shaking at room temperature for 1 hour or covered therewith at 4° C. overnight, and then washed with the rinse buffer three times. Subsequently, the slices were reacted with the primary antibody (table 1) diluted to proper concentration at room temperature for 2 hours or reacted therewith at 4° C. under shaking overnight, and then washed with the rinse buffer three times. Further, the slices were reacted with the secondary antibody at room temperature for 15 minutes, and then washed with the rinse buffer three times. Furthermore, the slices were reacted with the tertiary antibody at room temperature for 15 minutes, and then washed with the rinse buffer three times. DAB (LSAB2 Kit, DAKO, CA, USA) was added and then the slices were taken out when they were colored reddish brown (positive results). However, if no color appeared on the slices after 10 minutes, it indicated negative results. Then, the slices were immersed in ddH$_2$O to stop color reaction, and then stained with hematoxyline for 30 seconds to reveal nuclei of the tissue for contrast staining. Finally, the slices were immersed in flowing water for 10 minutes to cease reaction. After the stained slices were dried, they were sealed with gum arabic for photographing by microscopy.

TABLE 1

| Antibody | Function | Dilution | Source |
| --- | --- | --- | --- |
| anti-GFAP | Belonging to an intermediate filament protein and being specific to astrocytes of central nervous system (CNS) and used as a biomarker of neuroglia cells in neuronal differentiation. | 1:100 | Cell Signaling Technology |
| anti-Neu-N | Being a neuron-specific nucleoprotein and belonging to a marker of neurons. | 1:100 | Chemicon |
| anti-Caspase-3 | Being an apoptotic protein and belonging to a marker of apoptosis. | 1:100 | Cell Signaling Technology |

FIG. 1 shows proliferation of neuroglia cells, in which (A) is a normal group (sham), (B) is a control group, and (C) and (D) show the experimental group fed with an extract of Example 1. In FIG. 1, reddish brown indicates positive result and cyanosis indicates cell nuclei. As shown in FIG. 1, the group fed with the extract of Example 1 has reduced expression of GFAP. This means the proliferation of neuroglia cell is slowed down. Accordingly, the extract of the present invention can decrease the proliferation of neuroglia cell caused by ischemia because of brain artery infarction.

Figure 2:
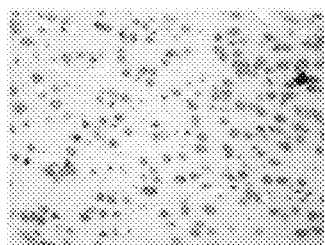
FIG. 2 is an immunohistochemistry photograph of neuronal nuclei (NeuN) protein showing proliferation condition of neuroglia cells, in which (A) shows a normal group, (B) shows a control group, and (C) and (D) show the group fed with an extract of Example 1; and reddish brown indicates positive result and cyanosis indicates cell nuclei.
Figure 2:
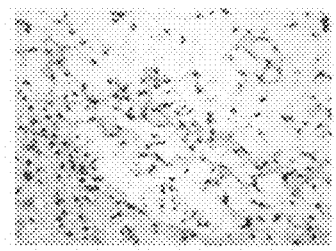
Figure 2:
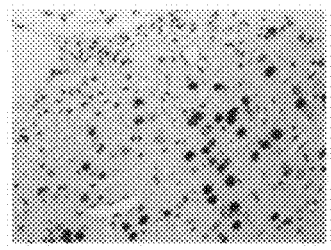
Figure 2:
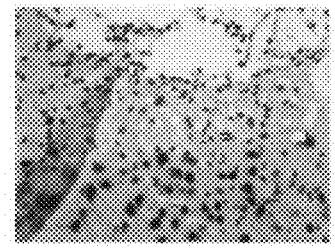

FIG. 2 also shows proliferation of neuroglia cells, in which (A) is a normal group (sham), (B) is a control group, and (C) and (D) shows the experimental group fed with an extract of Example 1. In FIG. 2, reddish brown indicates positive result and cyanosis indicates cell nuclei. As shown in FIG. 2, the group fed with the extract of Example 1 has increased expression of NeuN protein. This means the proliferation of neuroglia cell is slowed down. Accordingly, the extract of the present invention can promote the proliferation of neurons after brain artery infarction.

Figure 3:
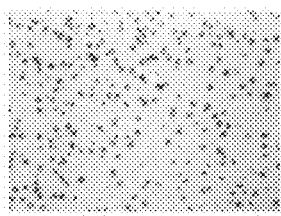
FIG. 3 is an immunohistostaining photograph of caspase-3 showing apoptotic condition of peripheral cells, in which (A) shows a normal group, (B) shows a control group, and (C), (D), and (E) show the group fed with an extract of Example 1; and reddish brown indicates positive result and cyanosis indicates cell nuclei.
Figure 3:
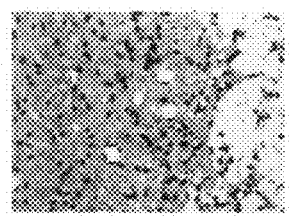
Figure 3:
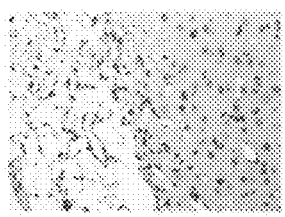
Figure 3:
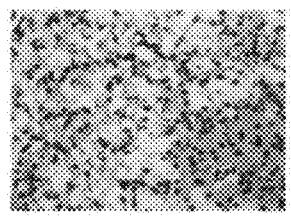
Figure 3:
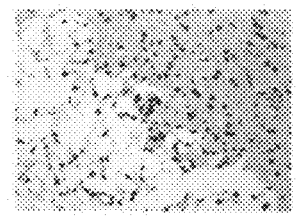

FIG. 3 shows apoptosis of peripheral cells, in which (A) shows a normal group, (B) shows a control group, and (C), (D), and (E) show the group fed with an extract of Example 1. In FIG. 3, reddish brown indicates positive result and cyanosis indicates cell nuclei. As shown in FIG. 3, the group fed with the extract of Example 1 has significantly decreased expression of caspase-3. This means the apoptosis of the peripheral cells is slowed down. Accordingly, the extract of the present invention can inhibit the apoptosis caused by ischemia because of brain artery infarction.

In conclusion, the expression of GFAP is actually increased in the peripheral cells of the brain infarction area after the rats are treated by ligation of right middle cerebral artery (MCA). However, after the animals are fed with the extract of Example 1, the expression of GFAP is significantly reduced in the peripheral cells of the brain infarction area and the expression of NeuN protein is remarkably increased. Hence, the herbal medicinal composition and extract of the present invention can be used to repair the brain lesion caused by infarction of right middle cerebral artery and simultaneously promote proliferation of neurons in the injured brain. Moreover, it is found that the expression of caspase-3 is inhibited in the peripheral cells near brain lesions. This means the herbal medicinal composition and extract of the present invention may alleviate brain lesions of cerebral artery infarction by inhibiting apoptosis of the peripheral cells near the ischemic areas.

Although the present invention has been explained in relation to its preferred embodiment, it is to be understood that many other possible modifications and variations can be made without departing from the scope of the invention as hereinafter claimed.

What is claimed is:

1. A herbal medicinal composition for inducing proliferation of cranial nerve cells, said composition comprising: 1.5-6 parts by weight of Salviae Radix, 1.5-6 parts by weight of Atractylodis Rhizoma, 1.5-6 parts by weight of *Poria*, 1.5-6 parts by weight of Glycyrrhizae Radix, 1.5-6 parts by weight of Angelicae Radix, 1.5-6 parts by weight of Paeoniae Radix Rubra, 1.5-6 parts by weight of Ligustici Rhizoma, 1.5-6 parts by weight of Rehmanniae Radix, 2.5-10 parts by weight of Aconiti Tuber, 1.5-6 parts by weight of Zingiberis Rhizoma, 1.5-6 parts by weight of Scutellariae Radix, 2.5-10 parts by weight of Cinnamon Seed, 10-40 parts by weight of Astragali Radix, 1.5-6 parts by weight of Cinnamomi Ramulus, and 1.5-6 parts by weight of Ginseng Radix.

2. The herbal medicinal composition as claimed in claim 1, wherein the Salviae Radix is in an amount of 2.25-4.5 parts by weight; the Atractylodis Rhizoma is in an amount of 2.25-4.5 parts by weight; the *Poria* is in an amount of 2.25-4.5 parts by weight; the Glycyrrhizae Radix is in an amount of 2.25-4.5 parts by weight; the Angelicae Radix is in an amount of 2.25-4.5 parts by weight; the Paeoniae Radix Rubra is in an amount of 2.25-4.5 parts by weight; the Ligustici Rhizoma is in an amount of 2.25-4.5 parts by weight; the Rehmanniae Radix is in an amount of 2.25-4.5 parts by weight; the Aconiti Tuber is in an amount of 3.75-7.5 parts by weight; the Zingiberis Rhizoma is in an amount of 2.25-4.5 parts by weight; the Scutellariae Radix is in an amount of 2.25-4.5 parts by weight; the Cinnamon Seed is in an amount of 3.75-7.5 parts by weight; the Astragali Radix is in an amount of 15-30 parts by weight; the Cinnamomi Ramulus is in an amount of 2.25-4.5 parts by weight; and the Ginseng Radix is in an amount of 2.25-4.5 parts by weight.

3. A method for manufacturing a herbal medicinal extract for inducing proliferation of cranial nerve cells, said method, comprising the following steps:

mixing 1.5-6 parts by weight of Salviae Radix, 1.5-6 parts by weight of Atractylodis Rhizoma, 1.5-6 parts by weight of *Poria*, 1.5-6 parts by weight of Glycyrrhizae Radix, 1.5-6 parts by weight of Angelicae Radix, 1.5-6 parts by weight of Paeoniae Radix Rubra, 1.5-6 parts by weight of Ligustici Rhizoma, 1.5-6 parts by weight of Rehmanniae Radix, 2.5-10 parts by weight of Aconiti Tuber, 1.5-6 parts by weight of Zingiberis Rhizoma, 1.5-6 parts by weight of Scutellariae Radix, 2.5-10 parts by weight of Cinnamon Seed, 10-40 parts by weight of Astragali Radix, and 1.5-6 parts by weight of Cinnamomi Ramulus to form a mixture; and extracting the mixture with water under heating to give an extract and then mixing the extract with 1.5-6 parts by weight of Ginseng Radix.

4. The method as claimed in claim 3, wherein the Salviae Radix is in an amount of 2.25-4.5 parts by weight; the Atractylodis Rhizoma is in an amount of 2.25-4.5 parts by weight; the *Poria* is in an amount of 2.25-4.5 parts by weight; the Glycyrrhizae Radix is in an amount of 2.25-4.5 parts by weight; the Angelicae Radix is in an amount of 2.25-4.5 parts by weight; the Paeoniae Radix Rubra is in an amount of 2.25-4.5 parts by weight; the Ligustici Rhizoma is in an amount of 2.25-4.5 parts by weight; the Rehmanniae Radix is in an amount of 2.25-4.5 parts by weight; the Aconiti Tuber is in an amount of 3.75-7.5 parts by weight; the Zingiberis Rhizoma is in an amount of 2.25-4.5 parts by weight; the Scutellariae Radix is in an amount of 2.25-4.5 parts by weight; the Cinnamon Seed is in an amount of 3.75-7.5 parts by weight; the Astragali Radix is in an amount of 15-30 parts by weight; the Cinnamomi Ramulus is in an amount of 2.25-4.5 parts by weight; and the Ginseng Radix is in an amount of 2.25-4.5 parts by weight.

5. A herbal medicinal extract for inducing proliferation of cranial nerve cells, wherein said extract is prepared by the following steps: mixing 1.5-6 parts by weight of Salviae Radix, 1.5-6 parts by weight of Atractylodis Rhizoma, 1.5-6 parts by weight of *Poria*, 1.5-6 parts by weight of Glycyrrhizae Radix, 1.5-6 parts by weight of Angelicae Radix, 1.5-6 parts by weight of Paeoniae Radix Rubra, 1.5-6 parts by weight of Ligustici Rhizoma, 1.5-6 parts by weight of Rehmanniae Radix, 2.5-10 parts by weight of Aconiti Tuber, 1.5-6 parts by weight of Zingiberis Rhizoma, 1.5-6 parts by weight of Scutellariae Radix, 2.5-10 parts by weight of Cinnamon Seed, 10-40 parts by weight of Astragali Radix, and 1.5-6 parts by weight of Cinnamomi Ramulus to form a mixture; and extracting the mixture with water under heating to give an extract and then mixing the extract with 1.5-6 parts by weight of Ginseng Radix.

6. The herbal medicinal extract as claimed in claim 5, wherein the Salviae Radix is in an amount of 2.25-4.5 parts by weight; the Atractylodis Rhizoma is in an amount of 2.25-4.5 parts by weight; the *Poria* is in an amount of 2.25-4.5 parts by weight; the Glycyrrhizae Radix is in an amount of 2.25-4.5 parts by weight; the Angelicae Radix is in an amount of 2.25-4.5 parts by weight; the Paeoniae Radix Rubra is in an amount of 2.25-4.5 parts by weight; the Ligustici Rhizoma is in an amount of 2.25-4.5 parts by weight; the Rehmanniae Radix is in an amount of 2.25-4.5 parts by weight; the Aconiti Tuber is in an amount of 3.75-7.5 parts by weight; the Zingiberis Rhizoma is in an amount of 2.25-4.5 parts by weight; the Scutellariae Radix is in an amount of 2.25-4.5 parts by weight; the Cinnamon Seed is in an amount of 3.75-7.5 parts by weight; the Astragali Radix is in an amount of 15-30 parts by weight; the Cinnamomi Ramulus is in an amount of 2.25-4.5 parts by weight; and the Ginseng Radix is in an amount of 2.25-4.5 parts by weight.

* * * * *